United States Patent [19]

Kranz

[11] Patent Number: 4,919,678

[45] Date of Patent: Apr. 24, 1990

[54] HIP JOINT PROSTHESIS HAVING A CYLINDRICAL SHAFT PORTION

[75] Inventor: Curt Kranz, Berlin, Fed. Rep. of Germany

[73] Assignee: MECRON medizinische Produkte GmbH, Berlin, Fed. Rep. of Germany

[21] Appl. No.: 205,883

[22] Filed: Jun. 13, 1988

[30] Foreign Application Priority Data

Jun. 12, 1987 [DE] Fed. Rep. of Germany ... 8708500[U]

[51] Int. Cl.$^5$ ................................................ A61F 2/32
[52] U.S. Cl. .......................................... 623/23; 606/63
[58] Field of Search ........................ 623/16, 18, 19, 20, 623/21, 22; 128/92 YY, 92 Y, 92 YZ, 92 YF

[56] References Cited

FOREIGN PATENT DOCUMENTS

| 0086879 | 8/1983 | European Pat. Off. | 623/18 |
| 0170982 | 2/1986 | European Pat. Off. | 623/22 |
| 179626 | 4/1986 | European Pat. Off. | 623/23 |
| 0204919 | 12/1986 | European Pat. Off. | 623/23 |

Primary Examiner—Richard J. Apley
Assistant Examiner—David Isabella
Attorney, Agent, or Firm—Spencer & Frank

[57] ABSTRACT

A hip joint prosthesis includes a first member having a shaft portion and a lateral arm extending toward a joint, the lateral arm being sloped in the direction of the joint and being adapted to receive a joint ball. The lateral arm has significantly greater length in a region adjacent the shaft and measured therealong than its corresponding thickness. A second member can be pushed onto the shaft portion supporting the lateral arm. This second member receives a distal end of the first member, with the second member essentially completely receiving the shaft portion supporting the lateral arm. The first member is joined at its proximal end to a proximal end of the second member. The lateral arm extends through a slit portion in the second member such that the region of the lateral arm adjacent the shaft portion is disposed within the slit portion.

15 Claims, 1 Drawing Sheet

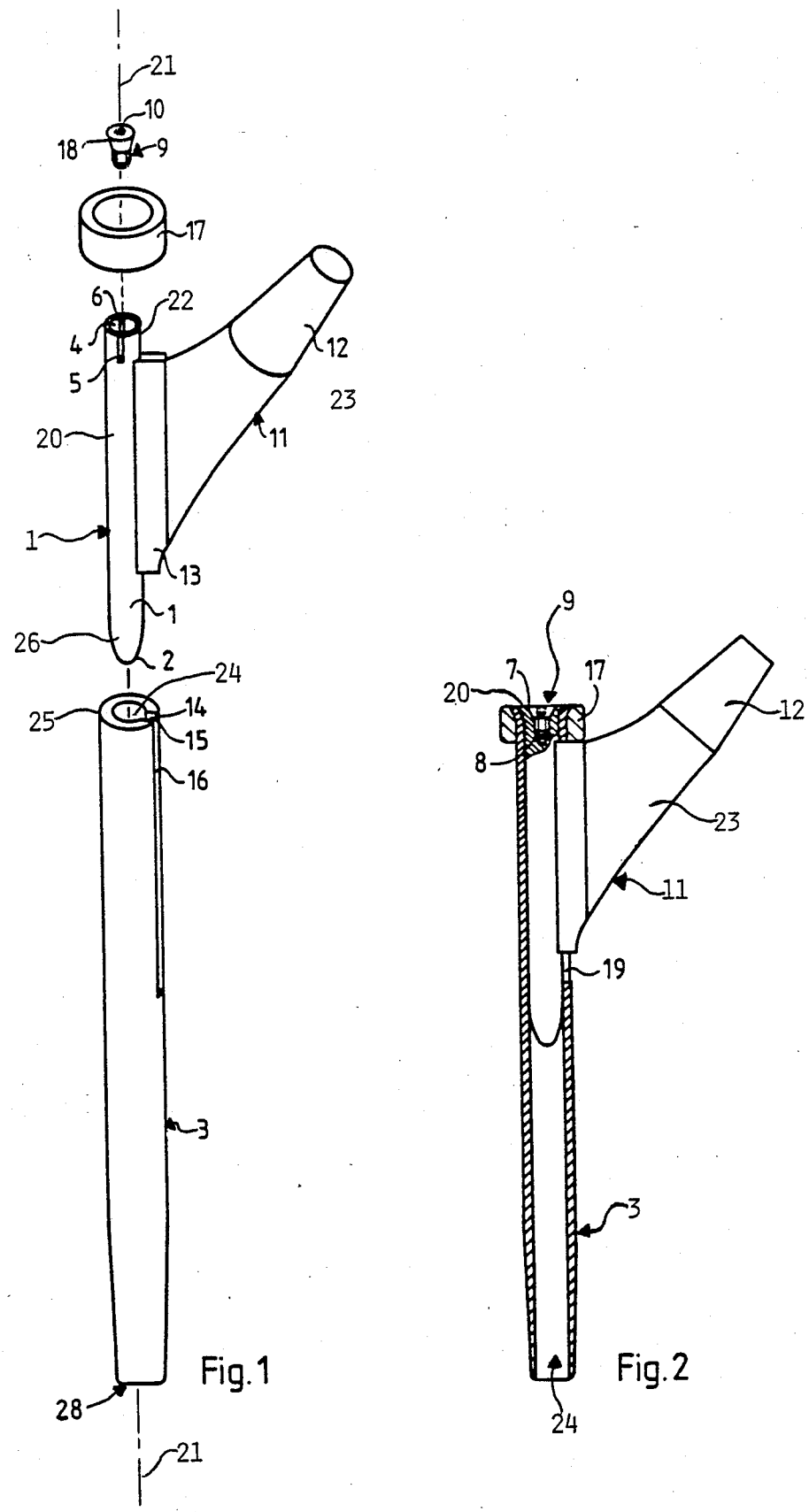

HIP JOINT PROSTHESIS HAVING A CYLINDRICAL SHAFT PORTION

BACKGROUND OF THE INVENTION

The present invention relates to a hip joint prosthesis having an essentially cylindrical first shaft member disposed in the vicinity of its end near the joint, the first shaft member being provided with a lateral arm oriented at an angle in the direction of the end for receiving the joint ball, wherein in its region adjacent the shaft, the dimension of the arm is substantially larger than in a direction which is tangential to the shaft; and a second shaft member can be pushed onto the member supporting the arm so as to project beyond the first member in the direction away from the joint end.

A hip joint prosthesis of this type is disclosed in published European Patent Application No. 179,626. In this prosthesis a conical shaft extends from an arm portion which has a joint ball. The conical shaft can be extended by separate members that can be pushed onto its end. It is a drawback of this arrangement that, particularly if longer shaft lengths are involved, instabilities may develop because the overlapping of successive elements is limited to the region of a cone end portion of the conical shaft. If several extensions are employed (corresponding to known "modular prostheses"), several extension elements and their associated conical connections would be required. Additionally, the mass of the shaft is considerable, particularly for longer lengths.

SUMMARY OF THE INVENTION

It is an object of the invention to provide a hip joint prosthesis of the above-mentioned type in which exchangeable parts can be produced at relatively little manufacturing expense to create a variable system of prostheses which have a relatively large rigidity and a relatively small mass.

The above and other objects are accomplished according to the invention by the provision of a hip joint prosthesis including:

(a) a first member having a generally cylindrical shaft portion having a longitudinal axis, the first member having a lateral arm extending at an angle, the lateral arm having a terminal end adapted for receiving a joint ball, wherein in a region adjacent the shaft portion, the lateral arm having a length in a direction parallel to the longitudinal axis and a width in a direction tangential to the shaft portion, the length being substantially larger than the width;

(b) a second member having a generally longitudinal slit therein, the second member being adapted for receiving the shaft portion such that the arm projects through the slit of the second member;

(c) in an assembled condition, the second member being substantially completely disposed about the shaft portion supporting the arm;

(d) connecting means for fixedly connecting an end of the shaft portion to an end of the second member such that the arm extends through the slit in the second member with the region of the arm adjacent the shaft portion being in the slit.

A particular advantage of the prosthesis according to the present invention is that one of the components, which must be manufactured in a forging die, can be made identical for each prosthesis of a system employing different shaft lengths, while the other components can preferably be manufactured from a tubular material as semi-finished products.

BRIEF DESCRIPTION OF THE DRAWINGS

FIG. 1 is an exploded perspective view of a preferred embodiment of a prosthesis according to the invention.

FIG. 2 is a partially sectional elevational view of the assembled embodiment according to FIG. 1.

DESCRIPTION OF THE PREFERRED EMBODIMENT

FIG. 1 illustrates an exploded view of a hip joint prosthesis, showing a first member 1 which has a generally cylindrical shaft portion 20 and a lateral arm 11 (hereafter referred to as arm 11). The shaft portion 20 can also have a conical or prismatic three-dimensional shape. The shaft portion 20 has a distal end portion 2 remote from a joint (not shown) and a proximal end portion 22. The end portion 2 has a rounded taper to facilitate insertion of the first member 1 into a second member 3. The second member 3 has a generally tubular hollow body, an interior 24, a proximal end 25, a distal end 28, and, in common with the shaft portion 20, a longitudinal axis 21.

At the proximal end portion 22, disposed at an upper end of the shaft portion 20 (near the joint), the first member 1 is provided with a bore 4. The shaft portion 20 is provided with slits 5 and 6, which are disposed on opposite sides of the bore 4. As shown in FIG. 2, an upper region of the bore 4 has a conically widened portion 7 and, at an adjacent lower region of the bore 4 itself, an internal thread 8 is formed in the shaft portion 20.

A screw 9 has a head portion 18 and a hexagonal recess 10. The screw 9 can be inserted into the threaded bore 8 to spread open the upper end of member 1 by tightening of the screw 9 by an Allen wrench fitting into the recess 10. The arm 11 has a cone portion 12 onto which a joint ball (not shown) can be pushed. The joint ball can be selected from an assortment of different ball sizes according to the patient's individual requirements.

Adjacent the shaft portion 20, the arm 11 has an arm portion 13 which has a relatively small thickness as measured in a tangential direction (with respect to the shaft portion 20), while its extent along the longitudinal direction of the shaft portion 20 is considerably larger in comparison thereto. In the vicinity of the shaft portion 20, the arm portion 13 of the arm 11 has a body which has two mutually oppositely located plane parallel faces which, when assembled together with the second member 3, engagingly contacts a pair of opposed side faces 14 and 15 of a slit 16 which is disposed longitudinally along the second member 3, the slit 16 thereby forming a guide for the first member 1 during assembly.

The arm 11 has a generally smoothly curving body which forms a transition region 23 which has a generally circular cross-sectional shape at a region adjacent the cone portion 12, and a smooth shape transition is made along the arm 11 until the arm 11 meets the elongated arm portion 13 which has a generally rectangular cross-sectional shape. For purposes of discussion of the preferred relative dimensions of the arm portion 13, an ellipse will therefore be defined by passage of a plane parallel to the longitudinal axis of the shaft portion 20 and through the substantially cylindrical portion of the transition region 23 of the arm 11 adjacent the cone portion 12, without passing through any part of the cone portion 12. The ellipse—not illustrated—has a major axis and a minor axis. These major and minor axes have respective lengths which are double the length of the corresponding major and minor half-axes. The longitudinal length of the portion 13 (as measured in a direction which is parallel to the longitudinal axis 21 along that region of the arm portion 13 which is adjacent to the shaft portion 20) is larger than the length of the major half-axis of the abovedescribed ellipse.

During assembly, the first member 1 is fastened to the second member 3 as follows: The shaft portion 20 is inserted into the hollow interior 24 of the second member 3 such that the arm 11 projects through the slit 16. As the shaft portion 20 is being pushed into the hollow interior 24, the arm portion 13 engages the walls 14 and 15 of the slit 16. When the proximal end portion 22 of the shaft portion 20 is adjacent the proximal end 25 of the second member 3, a securing means 17 (hereafter referred to as a clamping ring 17) is inserted on the proximal end 25. Then, the screw 9 is inserted into the bore 4 and is screwed into the internal thread 8 of the bore 4. An exterior surface of the head region 18 of the screw 9 has a conically widened portion, referred to hereafter as an outer cone. To secure the first member 1 and the second member 3 together, as the screw 9 is turned in the bore 4 of the first member 1, the outer cone of the head region 18 of the screw 9 engages with the conical region 7 of the bore 4 (the conical region 7 having a shape which will be referred to hereafter as an inner cone). By the action of screwing in of the screw 9 into the bore 4, the proximal end portion 22 of the first member 1 is spread open, the spreading operation being facilitated by the presence of the slits 5 and 6, such that an upper sleeve-shaped region of the second member 3 is pressed against an inner wall of the clamping ring 17 and thereby produces a clamped connection.

Due to the fact that the slit 16 has a length which is greater than the length of the arm portion 13 measured parallel to the axis 21, a gap 19 exists therebetween, as seen in FIG. 2. Therefore, the first member 1 can be adjusted along its longitudinal axis 21 within the second member 3 even after the second member 3 has already been fastened in a bone marrow region of a femur (not shown). Since the screw 9 is accessible from the top, the clamping ring 17 can be removed and the first member 1 can be adjusted relative to the second member 3. If repeat surgery is required at a later date, the second member 3 is still accessible from the top, and after the first member 1 has been removed, the second member 3 can be grasped and removed without great difficulty in view of the substantially linear and generally cylindrical shape of the hollow interior 24 and the corresponding generally cylindrical shape of the shaft portion 20 of the first member 1. The first member 1 can be replaced if desired, for example by a corresponding element which is longer or shorter. Although a cylindrical shape has been described and shown for the exterior surface of the shaft portion of the member 1 and for the hollow interior 24 of the second member 3, any cross-sectional shape could be used for the shaft portion 20 provided that the hollow interior 24 have a corresponding cross-sectional shape adapted for receiving the shaft portion 20 therein.

In other variations of the invention in a prosthesis system, the second member 3 may also preferably be provided in the form of a Küntscher nail (which has a throughgoing slit in its longitudinal direction) so that the advantages of nailing in the marrow region with such a nail can be combined with the advantages of the hip joint prosthesis disclosed herein.

The present disclosure relates to the subject matter disclosed in the German Application No. G 87 08 500.3 of June 12th, 1987, the entire specification of which is incorporated herein by reference.

It will be understood that the above description of the present invention is susceptible to various modifications, changes and adaptations, and the same are intended to be comprehended within the meaning and range of equivalents of the appended claims.

What is claimed is:

1. A hip joint prosthesis, comprising:
a first member having a shaft portion having a longitudinal axis, said first member having a lateral arm extending at an angle relative to said longitudinal axis, said lateral arm having a terminal end adapted for receiving a joint ball, wherein in a region adjacent said shaft portion said lateral arm has a length in a direction parallel to said longitudinal axis and a width in a direction tangential to said shaft portion, said length being substantially larger than said width;
a second member having a substantially tubular body which has a proximal end having a hollow interior, said proximal end of said second member having a generally longitudinally disposed slit therein, said slit portion being relatively narrow in width relative to a peripheral circumferential extent of said substantially tubular body adjacent said slit, said hollow interior of said proximal end of said second member being adapted for receiving said shaft portion of said first member such that said lateral arm projects through said slit in said second member;
in an assembled condition, said shaft portion of said first member being substantially completely disposed within said hollow interior of said proximal end of said second member and being substantially completely surrounded by said tubular body, and said region of said lateral arm adjacent said shaft portion being disposed in said slit; and
connecting means for fixedly connecting a proximal end of said shaft portion to a proximal end of said second member while said first and second members are in said assembled condition.

2. A hip joint prosthesis as defined in claim 1, wherein said connecting means comprises securing means which engages said second member for securing said proximal end of said second member to said proximal end of said first member.

3. A hip joint prosthesis as defined in claim 1, wherein said second member is a substantially entirely hollow body.

4. A hip joint prosthesis as defined in claim 1, wherein a distal end of said second member is conically tapered.

5. A hip joint prosthesis as defined in claim 4, wherein said hollow body of said second member is composed of a sheet metal.

6. A hip joint prosthesis as defined in claim 1, wherein said second member is a generally tubular body containing said longitudinal slit and wherein said longitudinal slit extends completely along the entire longitudinal extent of said generally tubular body, whereby said generally tubular body has an open cross-sectional shape throughout.

7. A hip joint prosthesis, comprising:

a first member having a shaft portion having a longitudinal axis, said first member having a lateral arm extending at an angle relative to said longitudinal axis, said lateral arm having a terminal end adapted for receiving a joint ball, wherein in a region adjacent said shaft portion, said lateral arm having a length in a direction parallel to said longitudinal axis and a width in a direction tangential to said shaft portion, said length being substantially larger than said width;

a second member having a proximal end having a hollow interior, said proximal end of said second member having a generally longitudinally disposed slit portion therein, said hollow interior of said proximal end of said second member being adapted for receiving said shaft portion of said first member such that said lateral arm projects through said slit portion in said second member;

in an assembled condition, said shaft portion of said first member being substantially completely disposed within said hollow interior of said proximal end of said second member, and said region of said lateral arm adjacent said shaft portion being disposed in said slit portion; and connecting means for fixedly connecting a proximal end of said shaft portion to a proximal end of said second member while said first and second members are in said assembled condition, said connecting means comprising securing means for contacting said second member for securing said proximal end of said second member to said proximal end of said first member, said securing means including a ring adapted for surrounding said proximal end of said second member and means for compressing said proximal end of said second member against said ring.

8. A hip joint prosthesis as defined in claim 7, wherein said ring is secured about said second member by a screw means when said screw means is engaged with said first member.

9. A hip joint prosthesis as defined in claim 8, wherein said screw means has a head portion that is conically widened in a direction of increasing distance from a threaded portion and engages in a recess in said proximal end of said first member, said proximal end of said first member being adapted for expanding upon insertion of said screw means.

10. A hip joint prosthesis having a portion which can be removed after installation in a patient for adjustment or replacement, comprising:

a first member having a shaft portion having a longitudinal axis, said first member having a lateral arm extending at an angle relative to said longitudinal axis, said lateral arm having a terminal end adapted for receiving a joint ball, wherein in a region adjacent said shaft portion said lateral arm has a length in a direction parallel to said longitudinal axis and a width in a direction tangential to said shaft portion, said length being substantially larger than said width;

a second member having a substantially tubular body which has a proximal end having a hollow interior, said second member having a specified length along said longitudinal axis, said proximal end of said second member having a generally longitudinal disposed slit therein in communication with said hollow interior, said slit having a predetermined length which is substantially less than said specified length of said second member and said slit being relatively narrow in width relative to a peripheral circumferential extent of said substantially tubular body, said hollow interior of said proximal end of said second member being adapted for receiving said shaft portion of said first member such that said lateral arm projects through said slit in said second member;

in an assembled condition, said shaft portion of said first member being substantially completely disposed within said hollow interior of said proximal end of said second member and being substantially completely surrounded by said tubular body, and said region of said lateral arm adjacent said shaft portion being disposed in said slit; and releasable connecting means for selectively fixedly connecting a proximal end of said shaft portion to a proximal end of said second member while said first and second members are in said assembled condition; whereby said first member can be removed from said assembled condition by release of said releasable connecting means.

11. A hip joint prosthesis as defined in claim 10, wherein said releasable connecting means comprises a securing means for engaging said second member for securing said proximal end of said second member to said proximal end of said first member.

12. A hip joint prosthesis as defined in claim 10, wherein said second member is a substantially entirely hollow body.

13. A hip joint prosthesis as defined in claim 12, wherein said hollow body of said second member is composed of sheet metal, and said slit has a length such that, in said assembled condition, said slit terminates at a location adjacent said lateral arm.

14. A hip joint prosthesis as defined in claim 10, wherein a distal end of said second member is conically tapered.

15. A hip joint prosthesis as defined in claim 10, wherein said second member is a generally tubular body containing said longitudinal slit and wherein said longitudinal slit extends completely along the entire longitudinal extent of said generally tubular body, whereby said generally tubular body has an open cross-sectional shape throughout.

* * * * *